United States Patent [19]

Utsuo et al.

[11] 4,089,333
[45] May 16, 1978

[54] METHOD OF TREATING A WOUND OR BURN

[75] Inventors: Akira Utsuo; Katsumi Matsutomo, both of Tokyo, Japan

[73] Assignee: Nippi, Incorporated, Tokyo, Japan

[21] Appl. No.: 698,336

[22] Filed: Jun. 22, 1976

Related U.S. Application Data

[60] Continuation-in-part of Ser. No. 594,719, Jul. 7, 1975, abandoned, which is a division of Ser. No. 399,447, Sep. 20, 1973, abandoned.

[30] Foreign Application Priority Data

Oct. 28, 1972 Japan .............................. 47-108322

[51] Int. Cl.$^2$ ............................................. A61L 15/00
[52] U.S. Cl. .............................. 128/156; 128/DIG. 8

[58] Field of Search ......... 128/149, 155, 156, DIG. 8, 128/296, 334

[56] References Cited

U.S. PATENT DOCUMENTS

| 3,063,781 | 11/1962 | Fetscher et al. | 128/DIG. 8 |
| 3,739,773 | 6/1973 | Schmitt et al. | 128/DIG. 8 |
| 3,810,473 | 5/1974 | Cruz et al. | 128/334 |

*Primary Examiner*—Lawrence W. Trapp
*Attorney, Agent, or Firm*—Hans Berman

[57] ABSTRACT

Method of treating a wound or burn which comprises directly dressing its surface with non-woven fabric comprising staple fibers of spun, regenerated collagen substantially free of telopeptides is disclosed.

6 Claims, No Drawings

METHOD OF TREATING A WOUND OR BURN

CROSS REFERENCE TO RELATED APPLICATIONS

This application is a continuation-in-part application of the abandoned U.S. patent application Ser. No. 594,719 which was filed on July 7, 1975 as a divisional application of abandoned application Ser. No. 399,447 filed on Sept. 20, 1973.

BACKGROUND OF THE INVENTION

1. Field of the Invention

This invention relates to a method of treating a wound or burn which comprises dressing the surface of the wound or burn to be treated directly with non-woven fabric of staple fibers of collagen substantially free of telopeptides. The non-woven fabric is prepared by cutting and tanning or tanning and cutting the regenerated spun collagen filament to form collagen staple fibers, forming non-woven fabric from said staple fibers, and optionally treating the non-woven fabric with a binder to bind the staple fibers to one another.

The method according to this invention is applicable to various wounds, such as injuries to the body in which skin or other tissue is broken, cut, pierced, torn and the like and to various body burns such as those caused by fire, hot liquid, steam, friction, acid and the like. The method according to this invention is realized with the use of other conventional articles for dresssing the surface of wound or burn.

2. Description of the Prior Art

Several materials have been proposed as skin substitute or as articles for dressing a wound or burn. Said materials include silicone gauze, Ivalon (formalized polyvinyl alcohol sponge), special fabrics — for example nylon velour, polyester, polypropylene, rayon or the like, and protein-coated specific fabrics, extremely thin silicon rubber film, fibrine film, case in film and cellulose film. However, these materials have not been successful in use.

Thiele et al. reported that a reconstituted collagen film from dispersion of swine skin brings about good result for this purpose. However, such film is not yet widely used and the process for making such film differs from the process for making the film of this invention. Namely, the Thiele film is prepared by subjecting the swine skin to fibrillation in water.

SUMMARY OF THE INVENTION

As a result of extensive research on dressings for treatment of various wounds and burns, it was found that a method of treating wounds and burns can be realized by the use of a non-woven fabric which is fabricated by staple fibers of spun, regenerated collagen substantially free of telopeptides.

DETAILED DESCRIPTION OF THE INVENTION

Collagen is the main protein constructing the skin of animals. It has been effectively used as a basic material for culture medium and, also, in recent years, collagen has been found to have many medical uses, for example, as a dialysis membrane, artificial cornea, artificial vitrei (vitreous body), surgical suture, artificial blood vessel and styptic sponge, and is being watched as a biomaterial having many advantages for applications in this field.

The term "spun collagen fiber" used herein defines a regenerated collagen fiber which is prepared by solubilizing collagen of an adult animal with the aid of a protease in acidic water (U.S. Pat. Nos. 3,034,852, No. 3,121,049 and No. 3,530,037) or by solubilizing the collagen with the aid of an amine, an alkali and sodium sulfate in water, thereafter acidifying the solution (U.S. Pat. No. 3,637,642) to obtain monomolecularly dispersed collagen solution, then forming the resulting solution into fiber and regenerating it.

It has long been known that a few percentages by weight of collagen in monomolecular form can be extracted from the skin of young animals by a dilute acid, a dilute alkali or a neutral salt solution. In general, such type of collagen is defined as "soluble collagen." On the other hand, collagen which can not be extracted by the above methods is called "insoluble collagen." The ratio of insoluble collagen to soluble collagen increases as an animal matures, and the skin of the substantially mature animal comes to comprise substantially insoluble collagen fiber.

The publications listed above relate to the method for solubilizing so-called insoluble collagen in water, and in accordance with the method almost 100% of insoluble collagen can be solubilized. The thus obtained collagen solution, in every case, is an aqueous solution in which collagen is dispersed in water in the form of monomolecules of rod-like double helical structure.

Various investigations have been carried out on the difference between insoluble and soluble collagens to prove the relationship of the ratio of the two types of collagen to aging of an animal from the viewpoint of the difference in molecular structure of the collagens.

It was found that collagen molecules solubilized in accordance with the method of the published inventions as listed above have no telopeptides extending at the end region of insoluble collagen molecules and that the protease or the amine used attacks the telopeptide moieties to cut them off without attacking the collagen molecule proper to maintain a stable double-helical structure.

Further, it has been observed that this telopeptidefree collagen does not exhibit significant antigenicity nor cause foreign body reaction when such collagen is applied to human body.

Thus, among known medical articles made from a collagenous material useful to treat wounds, the medical articles made of spun collagen fiber according to this invention do not exhibit antigenicity nor cause foreign body reaction thereby providing satisfactory compatibility with tissue. The article differs essentially from Thiele's article in biochemical characteristics.

On the basis of the characteristics of the collagenous non-woven fabric according to this invention, the article is expected to have an excellent effect as a dressing for wounds and burns. In fact, such excellent effect for treating wounds is confirmed by the results of clinical studies.

By the inventions relating to solubilization of the so-called insoluble collagen which were published as U.S. Patents listed above, collagen made from the skin of a mature animal can be solubilized to monomolecular form of collagen with almost 100% of yield. Therefore, the material for this invention can be prepared from various animals in an amount sufficient for industrial use.

Spun collagen fiber which may be used for making non-woven fabric of this invention can be prepared by the methods similar to that of the invention disclosed in Japanese Pat. Publication No. 9062/65.

The non-woven fabric can be prepared by preparing collagen solution according to enzyme process or amine process as mentioned above, extruding the solution through a spinneret into a concentrated neutral salt aqueous solution to form fiber, cutting the fiber to form staple and preparing non-woven fabric from the staple by a wet or dry process. To improve water-resistance of the product, the spun fiber is desirably treated with a tanning agent. Further, in order to improve the entaglement of the staple fibers, the fibrilization of spun fiber may be facilitated prior to making non-woven fabric, or the non-woven fabric may be subjected to conventional needle-punching work. Further, if necessary, the non-woven fabric may be treated with a binder such as an aqueous solution of undenatured collagen or denatured collagen such as gelatin to firmly bind the staple fibers to one another. However, if the fabric is subjected to treatment with the binder, the water resistance of the fabric is lowered and therefore, it is desirable to treat the fabric with a tanning agent after the treatment with the binder.

The non-woven fabric thus prepared is sterilized and wrapped by a conventional method.

The process of this invention is generally carried out as follows.

Preparation of Spun Collagen Fiber

Although the four processes for preparing spinning solution of collagen disclosed in the U.S. Patents mentioned above may be conveniently used, the process according to U.S. Pat. No. 3,530,037 is preferred to carry out this invention. A collagen solution of pH 2-4 and a collagen concentration in the range of 1 to 10% is used as a spinning solution. When the solution is prepared by the amine process, the pH thereof is adjusted to the range of 2 to 4 by the addition of an acid. The spinning solution is extruded through spinnerets into a coagulation bath of a saturated, aqueous neutral salt solution, the draw ratio of the fiber during coagulation being preferably 1.5 to 30. The spun fiber is dried at about 50° C. The diameter of the dried fiber which can be controlled by the selection of the extrusion conditions such as the concentration of the spinning solution, diameter of spinneret and the like is preferably 1.5 to 2.5 denier. As stated above, the spun collagen fiber is cut into staple when non-woven fabric is made. However, the length of the staple must be changed depending upon the use of a wet or dry process. When the dry process for preparing non-woven fabric is used, the length of the staple is usually 2.5-7.0 cm, preferably 5.0 cm, while in case of the wet process, the length is usually 0.2 to 1.0 cm, preferably 0.5 cm. Then the staple may be subjected to tanning treatment with aldehyde, for example formaldehyde or glutaraldehyde, or chromium tanning agent thereby improving the water resistance of the staple. The tanning treatment is believed to further reduce antigenicity and allergic reaction to the material. The tanning treatment may be carried out in an aqueous alkali solution of pH 8 to 10 when an aldehyde is used, or in an acid aqueous solution of pH 3.0-3.5 when a chromium tanning agent is used. A relatively large amount of a neutral salt must be present in both aqueous solutions. In the tanning step using an aldehyde, an aqueous solution may contain about 0.05-2.0% of formaldehyde or about 0.1 to 2.0% of glutaraldehyde. In the tanning step, a usual chromium tanning liquor may be used and HIGH NEOCHROME (Nippon Kagaku Kogyo Kabushiki Kaisha, Japan) is conveniently used in about a 0.3-10% aqueous solution. In both tanning steps, the treating time, is controlled as a matter of course; usually, 2 - 20 hours of the treating period with the solution at 30°-40° C is preferred. After the completion of tanning, the tanned staple is washed with running water for about 2 hours and dried at 50° to 60° C.

Alternately, this invention can be carried out by subjecting the spun collagen fiber to the tanning treatment and then cutting the tanned fiber into staple. In the process, conditions similar to those described above may be used.

After drying the staple, the amount of the tanning agent bound to collagen is 0.2-2.0% by weight of formaldehyde, 0.6-2.5% by weight of glutaraldehyde or 1.5 to 7.0% by weight of chrome as $Cr_2O_3$.

Preparation of Non-Woven Fabric

The non-woven fabric is formed from the thus prepared staple by either a wet or dry process. Any conventional dry process can be used to form the non-woven fabric of this invention, but a random webber may be conveniently used. The staple is supplied to an opener and then to a random webber to form non-woven fabric. The density of the thus formed fabric is preferably $0.01-0.02 g/cm^3$.

As in the wet process, the staple is supplied to a homogenizer, refiner or ball mill of alumina to subject it to fibrilization thereby forming a slurry. The staple content of the slurry is preferably 0.02-2.0%. If desired an aqueous solution of denatured or undenatured collagen is added to the slurry. The concentration of binder is 0.01-1.0%. Then the slurry is treated by a paper machine to form non-woven fabric.

In dry state, the fabric has a density of $0.05-0.4 g/cm^3$ and contains 2-20% by weight of the binder used.

The non-woven fabric prepared by the dry process according to this invention is then dipped into an aqueous solution which contains preferably about 0.2-1.5% of a binder; thereafter, the fabric is squeezed to remove excess solution. The binder bound to the fabric is preferably present in an amount of about 2-20% by weight based on the staple. After this treatment, the non-woven fabric is dried at a temperature of 50°-60° C. Just before drying, the fabric may be treated with a concentrated aqueous neutral salt solution to coagulate the binder applied thereto. If necessary, the fabric may be treated with a tanning agent to improve the water-resistance of the binder. When the fabric is treated with a concentrated aqueous neutral salt solution, the fabric may be treated with a tanning agent before drying. This treatment may be carried out under conditions essentially similar to those stated in the production of the staple.

The fabric thus obtained is cut into sheets of the desired size, allowed to stand in an atmosphere consisting of ethyleneoxide and carbondioxide at about 40° C under a pressure of about 2 atms for 5 hours to sterilize it and then wrapped.

The detailed conditions for the production of the non-woven fabric are further illustrated by the following description.

(1) Preparation of a collagen spinning solution

As a source of collagen, adult steer, cow or ox hide is preferred, because it is readily available as an industrial raw material. In addition to the hide, ossein comprising animal bones may also be used.

First of all, the hides are washed, and fleshed to obtain corium. The corium is immersed in aqueous 5% NaCl solution to remove soluble substances, then subjected to enzyme dehairing and cut into chips with a mincer. To 1,000g of the chips is added 10 liters of diluted hydrochloric acid to adjust the pH after equilibrium to 3. To the mixture is added 1.5g of Proctase (Meiji Seika Co.; an acid protease produced by *Aspergillus niger* and having an optimal pH of 2.0 against casein and 300,000 units to the substrate) and stirred at about 25° C for 24 hours to solubilize the chips. The solution is filtered to obtain a spinning solution. In the solution, collagen is monomolecularly dispersed. The spinning solution usually has a concentration from 1 to 10%, preferably from 2 to 6% of collagen. It is important to hold the pH of the solution at 3.0 and to store it at a temperature below 30° C until it is used.

(2) Production of collagen staple fibers

The spinning solution is extruded through a spinneret with 330 holes of 0.08 mm in diameter into a saturated, aqueous $Na_2SO_4$ solution of a pH from 3 to 4, at an extrusion rate of 10 cc/min. The revolutions of the take-up roller are controlled to give a running rate of the fiber of 15 m/min. and to give a draw ratio in the bath of about 2.5. The fiber is dried at 50°–60° C and cut into staple in the length as mentioned above. Then, the staple is treated with a tanning agent to improve water-resistance. Some examples of such treatment are shown in the following Table 1.

Table 1

|  | Runs | | | | | |
| --- | --- | --- | --- | --- | --- | --- |
|  | F-1 | F-2 | C-1 | C-2 | G-1 | G-2 |
| Formaldehyde (%) | 0.1 | 1.0 | — | — | — | — |
| High Neochrome (%) | — | — | 0.5 | 7.0 | — | — |
| Glutaraldehyde (%) | — | — | — | — | 0.17 | 1.7 |
| $Na_2SO_4$ (%) | 12.0 | 12.0 | 20.0 | 5.0 | 12.0 | 12.0 |
| $NaHCO_3$ (%) | 0.5 | 0.5 | — | — | 0.5 | 0.5 |
| $Na_2CO_3$ (%) | 0.1 | 0.1 | — | — | 0.1 | 0.1 |
| Water | 87.3 | 86.4 | 79.5 | 88.0 | 87.2 | 85.7 |
| pH | 8.5–9.5 | 8.5–9.0 | 3.4–3.8 | 2.7–3.3 | 8.5–9.5 | 8.5–9.5 |
| Temperature (° C) | 30 | 30 | 30–40 | 30–40 | 30 | 30 |
| Time for the treatment (hrs) | 2 | 20 | 20 | 3 | 2 | 20 |
| Time for the washing (hrs) | 2 | 2 | 2 | 2 | 2 | 2 |
| Amount of the binder bound (%) | F 0.5–0.8 | F 1.4–1.8 | $Cr_2O_3$ 1.5–3.5 | $Cr_2O_3$ 5.0–7.0 | G 0.6–0.9 | G 1.5–2.0 |

F: formaldehyde,
C: chromium-tanning agent,
G: glutaraldehyde.

EXAMPLE I 5 cm long staple which had been subjected to the tanning treatment according to F-1 in Table 1 was opened by the opener Model OP-200, Daiwa Kiko Kabushiki Kaisha (Japan) and then, treated by the random webber of the same company to form non-woven fabric. The density of the fabric was 0.01 g/cm³. Then, the fabric was dipped into a 10% aqueous solution of denatured collagen, squeezed and dried at 60° C. The dried fabric contained 15% by weight of the binder as solid. In order to improve water-resistance, the fabric was treated in the manner as shown in Table 2, F-1.

After drying, the fabric was cut into 10 cm × 10 cm sheets and they were placed in an autoclave equipped with a heat jacket and sterilized with CAPOX-20 (a mixed gas consisting of ethylene oxide and carbon dioxide in the ratio of 20:80) at 40° C 2 atms for 5 hours.

Table 2

|  | Runs | | | | | |
| --- | --- | --- | --- | --- | --- | --- |
|  | F-1 | F-2 | C-1 | C-2 | G-1 | G-2 |
| Formaldehyde (%) | 0.1 | 1.0 | — | — | — | — |
| High Neochrome (%) | — | — | 0.5 | 7.0 | — | — |
| Glutaraldehyde (%) | — | — | — | — | 0.17 | 1.7 |
| $Na_2SO_4$ (%) | 24.0 | 24.0 | 24.0 | 24.0 | 24.0 | 24.0 |
| $NaHCO_3$ (%) | 0.5 | 0.5 | — | — | 0.5 | 0.5 |
| $Na_2CO_3$ (%) | 0.1 | 0.1 | — | — | 0.1 | 0.1 |
| Water | 75.3 | 74.4 | 75.5 | 69.0 | 75.2 | 73.7 |
| pH | 8.5–9.5 | 8.5–9.5 | 3.4–3.8 | 2.7–3.3 | 8.5–9.5 | 8.5–9.5 |
| Temperature (° C) | 25–30 | 25–30 | 25–30 | 25–30 | 25–30 | 25–30 |
| Time for the treatment (hrs) | 2 | 20 | 20 | 2 | 2 | 20 |
| Time for the washing (hrs) | 2 | 2 | 2 | 2 | 2 | 2 |

EXAMPLE II

A non-woven fabric was formed by the method according to Example I, except that the staple had been subjected to the treatment by C-1 of Table 1. The fabric was dipped in a 0.5% aqueous collagen solution, squeezed, treated with a saturated $Na_2SO_4$ aqueous solution to coagulate the binder and then dried. The fabric contained 17% by weight of the binder. The fabric thus formed was tanned in the manner as shown in Table 2, C-1, then washed with water and dried. The fabric thus obtained was sterilized and wrapped in the same manner as described in Example I.

EXAMPLE III

Example II was repeated except that the tanning treatment was carried out after coagulation without drying. The fabric contained 17% by weight of the binder. The fabric was sterilized and wrapped in the same manner as described in Example II.

EXAMPLE IV

The non-woven fabric was prepared by a wet process from collagen staple fibers 0.5 cm long which had been tanned in the manner as described in Table 1, G-1. The aqueous slurry containing 1.0% (w/w) of the staple fibers was prepared by the use of the Universal Homogenizer (Nihon Seiki Seisaku-sho). An aqueous solution of denatured collagen was added to the slurry in an amount sufficient to provide a concentration of 1% of collagen in the slurry. Non-woven fabric was prepared from the slurry thus obtained with use of the TSS standard square-sheet machine (Toyo Seiki Seisaku-sho, Japan). After drying at a temperature of 60° C, the fabric was tanned in the manner as described in Table 2, G-1, and then dried. The fabric thus treated contained 15% of the binder. The fabric was cut into 10 cm × 10 cm sheets and they were sterilized and wrapped in the same manner as described in Example I.

EXAMPLE V

The non-woven fabric prepared by the dry process according to Example I was dipped in 1% denatured collagen aqueous solution then squeezed and dried. The dried fabric was tanned in the manner as described in Table 2, F-2, then cut and wrapped in the same manner as stated in Example I.

EXAMPLE VI

The spun collagen fiber which had been tanned in the same manner as described in Table 1, F-1 was cut into staple 0.3 cm long, and non-woven fabric was prepared by a wet process. Namely, the staple was dispersed in water to form a slurry of 5% of staple and the slurry was treated by the KRK type refiner for a high concentration slurry (Kumagaya Riki Kogyo Kabushiki Kaisha, Japan) to subject the staple to fibrilization. The thus treated slurry was diluted to a staple content of 0.5%. Thereafter, non-woven fabric was prepared from the slurry by the standard sheet machine of the same company and dried in air at room temperature. The thus obtained fabric was strong enough for use without use of a binder. The fabric was cut into 10 cm × 10 cm sheets and then the sheets were sterilized and wrapped in the same manner as described in Example I.

EXAMPLE VII

Spun collagen fiber which had been tanned in the same manner as shown in Table 1, G-2 was cut into staple 0.5 cm long and non-woven fabric was prepared by a wet process. The staple was dispersed in water to form a slurry of 5% of solid content. The slurry thus obtained was fed to a ball-mill of alumina to subject the staple to fibrilization. After adjusting the concentration of the staple to 0.1%, a collagen solution was added as a binder to the slurry in an amount sufficient to make the concentration of the binder 0.05%. From the slurry, non-woven fabric was prepared by a hand-sheet machine. The fabric was then tanned without drying in the same manner as shown in Table 2, G-2. The binder content of the fabric was 3% by weight. The fabric was cut into 10 cm × 10 cm sheets and the sheets were sterilized and wrapped in the same manner as described in Example I.

It was confirmed that each of non-woven fabrics according to Examples I through VII has an excellent therapeutic effect. In order to demonstrate the effect, the result of some Examples are shown as follows.

EXAMPLE VIII

Hair on the back of a rabbit was sheared and the place was disinfected. Under procaine anesthesia four 5 × 4 cm, 0.5-0.8 mm thick dermal injuries of the rabbit were surgically induced by a dermatome. Each of the two injuries was directly dressed with a non-woven fabric prepared in Example I and covered with sterilized gauze. The gauze was sewn to the skin to prevent the fabric from falling down. Finally, an elastic bandage was applied to the injuries.

As a control conventional nylon gauze containing fradiomycin was used for each of the other two injuries. One week after the operation, each of the injuries was observed with the naked eye to evaluate the rate and quality of incrustation.

The dressing of this invention had combined with body fluid to form a good crust. In contrast, on the control, the gauze was attached to the body and when the gauze was stripped off, bleeding was often observed.

EXAMPLE IX

Example VIII was repeated, except that the non-woven fabric prepared according to Example II was used instead of that according to Example I to give essentially the same results as shown in Example VIII.

EXAMPLE X

A deep abrasion on a board area of a patient's leg was treated, after excising the skin surrounding the abrasion, in the manner similar to that described in Example VIII with non-woven fabric prepared in accordance with Example VI. Five days after the treatment, the abrasion was observed to have good incrustation. Since the fabric applied was digested, there was no need to strip off the fabric after cure. When a piece of skin was trasplanted on the crust, the piece attached well to living tissue.

EXAMPLE XI

A 10 cm × 10 cm skin flap was grafted from the upper arm of a patient to a defect of the esophagus the neck. Ilotycin ointment was applied to the injury in the arm and then dressed with the fabric prepared in Example VII.

One week after the treatment, a good crust similar to that of Example X was observed. Since the fabric was digested, when the remaining portion of the flap was put back in its place, the flap was observed to attach well to living tissue.

As stated hereinbefore, the most important characteristic of the non-woven fabric according to this invention resides in that the non-woven fabric per se converts to crust by combining with body fluid. This is an effect which could not be provided with any prior art material. Such effect had not been obtained until the fabric made from collagen according to this invention was developed. In particular, since solubilized collagen which is prepared by treating collagenous material with the enzyme or the amine to digest telopeptides does not have essential antigenicity nor cause foreign body reaction, fabric made from such collagen adhered firmly to living tissue to promote a complete cure without leaving a scar.

In addition, the fabric of this invention is good in absorption of body fluid and in permeability to water vapor. Therefore, it functions like skin with respect to wounds. After cure of the wound, there is no need to strip the fabric and partial growth of hair was observed.

Although sponge and powder may be prepared from solubilized collagen and these articles may be used for therapeutic purpose, a fabric is far more convenient.

What is claimed is:

1. A method of treating a wound or burn which comprises directly dressing the surface of the wound or burn with a non-woven fabric essentially consisting of staple fibers of spun, regenerated collagen substantially free of telopeptides.

2. A method according to claim 1 wherein said non-woven fabric further comprises a binder binding said staple fibers to one another, said binder being a member of the group consisting of solubilized collagen and denatured collagen.

3. A method according to claim 2 wherein said staple fibers have a length of 0.2 to 7.0 cm, and the amount of said binder is 2 to 20 percent of the weight of said staple fibers.

4. A method according to claim 1 wherein said fibers are tanned with a tanning agent selected from the group consisting of formaldehyde, glutaraldehyde and chromium tanning agent.

5. A method according to claim 1 wherein said fabric has a bulk density of 0.01 to 0.02 gram per cubic centimeter.

6. A method according to claim 1 wherein said fabric has a bulk density of 0.05 to 0.4 gram per cubic centimeter.

* * * * *